(12) United States Patent
Janniello (10) Patent No.: US 12,403,054 B2
(45) Date of Patent: Sep. 2, 2025

(54) METHODS, SYSTEMS, AND APPARATUS FOR AN ADJUSTABLE BED FRAME BASED ON BIOMETRIC INFORMATION

(71) Applicant: James P Janniello, Sarasota, FL (US)

(72) Inventor: James P Janniello, Sarasota, FL (US)

( * ) Notice: Subject to any disclaimer, the term of this patent is extended or adjusted under 35 U.S.C. 154(b) by 693 days.

(21) Appl. No.: 16/894,876

(22) Filed: Jun. 7, 2020

(65) Prior Publication Data

US 2020/0383852 A1  Dec. 10, 2020

Related U.S. Application Data

(60) Provisional application No. 62/921,277, filed on Jun. 7, 2019.

(51) Int. Cl.
*A61G 7/018* (2006.01)
*A61B 5/00* (2006.01)
*G05B 19/402* (2006.01)

(52) U.S. Cl.
CPC ............ *A61G 7/018* (2013.01); *A61B 5/4809* (2013.01); *A61B 5/4818* (2013.01); *G05B 19/402* (2013.01); *A61G 2203/70* (2013.01); *G05B 2219/2608* (2013.01)

(58) Field of Classification Search
CPC .................................................. A61G 2203/70

USPC .......................................................... 700/60
See application file for complete search history.

(56) References Cited

U.S. PATENT DOCUMENTS

| | | | |
|---|---|---|---|
| 10,736,432 B2* | 8/2020 | Nunn ..................... | A47C 27/10 |
| 2003/0195644 A1* | 10/2003 | Borders ................ | A61G 12/00 |
| | | | 340/568.1 |
| 2007/0101500 A1* | 5/2007 | Fruh ...................... | A61G 13/08 |
| | | | 5/613 |
| 2007/0110448 A1* | 5/2007 | Ruch ...................... | G08C 23/04 |
| | | | 398/140 |
| 2011/0015495 A1* | 1/2011 | Dothie ................. | A47C 31/123 |
| | | | 600/300 |
| 2011/0224510 A1* | 9/2011 | Oakhill ................ | A61B 5/4815 |
| | | | 600/301 |
| 2012/0137436 A1* | 6/2012 | Andrienko ............. | G16Z 99/00 |
| | | | 5/600 |
| 2012/0138067 A1* | 6/2012 | Rawls-Meehan ...... | A47C 17/86 |
| | | | 5/616 |
| 2012/0324649 A1* | 12/2012 | Lin ....................... | A61B 5/0002 |
| | | | 5/613 |
| 2017/0135632 A1* | 5/2017 | Franceschetti ......... | A61B 5/725 |
| 2019/0206416 A1* | 7/2019 | Demirli .................. | H04L 67/10 |

* cited by examiner

*Primary Examiner* — Md Abul Azad (57) ABSTRACT

Methods, systems, and apparatus for configuring a bed frame are described. Biometric information corresponding to a user is obtained. A bed frame configuration is determined based on the biometric information and the bed frame is configured based on the determined bed frame configuration and the biometric information.

20 Claims, 4 Drawing Sheets

METHODS, SYSTEMS, AND APPARATUS FOR AN ADJUSTABLE BED FRAME BASED ON BIOMETRIC INFORMATION

CLAIM OF PRIORITY

This application claims the benefit of priority under 35 U.S.C. § 119(e) of U.S. Provisional Patent Application Ser. No. 62/921,277, filed on Jun. 7, 2019, which is incorporated by reference herein in its entirety.

TECHNICAL FIELD

The present application relates generally to electronic and mechanical arts, and more specifically, in one example, to an adjustable bed frame.

BACKGROUND

Proper sleep is known to have many health benefits. Snoring, sleep apnea, and other sleep maladies are known to interfere with a person's sleep, often resulting in a variety of health issues. In many cases, the sleep quality and instances of sleep apnea are related to the position of an individual's body during sleep, especially in regard to the position of an individual's air passages. Some individuals will not snore or suffer from sleep apnea when sleeping in a more vertical position, but may suffer from snoring, sleep apnea or both when sleeping in a horizontal position.

BRIEF DESCRIPTION OF THE DRAWINGS

Some embodiments are illustrated by way of example and not limitation in the figures of the accompanying drawings in which.

DETAILED DESCRIPTION

In the following detailed description of example embodiments, reference is made to specific examples by way of drawings and illustrations. These examples are described in sufficient detail to enable those skilled in the art to practice these example embodiments, and serve to illustrate how the invention may be applied to various purposes or embodiments. Other embodiments of the invention exist and are within the scope of the invention, and logical, mechanical, electrical, and other changes may be made without departing from the scope or extent of the present invention. Features or limitations of various embodiments of the invention described herein, however essential to the example embodiments in which they are incorporated, do not limit the invention as a whole, and any reference to the invention, its elements, operation, and application do not limit the invention as a whole but serve only to define these example embodiments. The following detailed description does not, therefore, limit the scope of the invention, which is defined only by the appended claims.

Generally, methods, systems, and apparatus for an adjustable bed frame are described. In one example embodiment, the bed frame is adjusted based on biometric information. For example, a pulse rate, a blood pressure measurement, an oxygen rate, a weight measurement, and the like of an individual may be used to adjust the bedframe. In one example embodiment, a microphone detects sounds emitted by an individual, such as sounds indicative of snoring, and the bed frame is adjusted based on the detected sounds to reduce the snoring. In one example embodiment, the bed frame is adjusted based on a lack of a detected sound. For example, the bed frame may be adjusted if no breathing sounds are detected, potentially indicating an episode of sleep apnea. The bed frame may be automatically adjusted to mitigate a sleep event, such as an episode of sleep apnea, and may be automatically adjusted when the sleep event ends to, for example, return the bed frame to a starting configuration.

Figure 1:
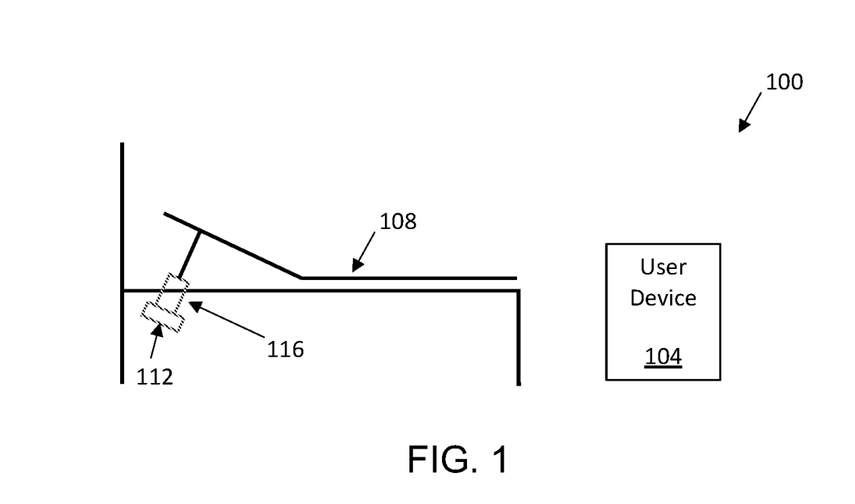
FIG. 1 is a block diagram of an example system for an adjustable bed frame, in accordance with an example embodiment.

FIG. 1 is a block diagram of an example system for an adjustable bed frame, in accordance with an example embodiment. In one example embodiment, the system 100 may comprise one or more user devices 104-1, 104-2 and 104-N (known as user devices 104 hereinafter), a bed frame 108, a bed frame controller 112, and a bed frame adjuster 116. In one example embodiment, the bed frame controller 112 incorporates a user interface mechanism. The user interface mechanism allows a user to directly control the system 100, allows the user to control the system 100 via the user device 104, or both.

Each user device (e.g., 104-1) may be a personal computer (PC), a tablet computer, a mobile phone, a personal digital assistant (PDA), a wearable computing device (e.g., a smartwatch), or any other appropriate computer device. Each user device (104-1, 104-2 or 104-N) may include a user interface processing module for providing a user interface, described more fully below in conjunction with FIG. 4. In one example embodiment, the user interface processing module may comprise a web browser program. Although a detailed description is only illustrated for user device 104-1, it is noted that each of the other user devices (e.g., user device 104-2 through user device 104-N) may have corresponding elements with the same functionality.

The bed frame 108 is an adjustable mechanical structure for supporting and adjusting a configuration of, for example, a mattress (not shown). The bed frame 108 may be configured in a variety of positions. In one example embodiment, the head of the bed frame 108 may be configured in the horizontal position, in the vertical position, or slanted a number of degrees between the horizontal and vertical positions. In one example embodiment, the head of the bed frame 108 and the foot of the bed frame 108 may be configured in the horizontal position, in the vertical position, or slanted a number of degrees between the horizontal and vertical positions. Other configurations of the bed frame 108 are also contemplated. For example, the bed frame 108 may comprise a plurality of horizontal slats that the enable the bed frame 108 to assume different shapes, such as bending at different points between the head and the foot on the bed frame 108. In one example embodiment, each slat is six inches in width and equal to the width of the mattress in length.

The bed frame controller 112 controls the configuration of the bed frame 108 based, for example, on biometric information of a user. The bed frame controller 112 controls the configuration of the bed frame 108 by sending control signals to the bedframe adjuster 116. For example, the bedframe adjuster 116 may send a command instructing the bedframe adjuster 116 to extend to a specified length, to configure the bed frame 108 based on a specified angle for a specified portion of the bed frame 108, and the like.

In one example embodiment, the bed frame controller 112 generates a user interface for configuring and controlling the system 100, including the bed frame controller 112. In one example embodiment, the bed frame controller 112 interfaces with the user device 104, and the user device 104 generates a user interface for configuring and controlling the system 100, including the bed frame controller 112, and exchanges control and status information with the bed frame controller 112.

The bed frame adjuster 116 mechanically configures and reconfigures the bed frame 108. In one example embodiment, an electrically-powered pneumatic piston of the bed frame adjuster 116 adjusts the slant of the head portion of the bed frame 108. In one example embodiment, a plurality of electrically-powered pneumatic pistons adjust the bed frame adjuster 116. For example, each piston may be coupled to a different portion of the bed frame 108 and independently configures the corresponding portion of the bed frame 108. In one example embodiment, each piston can be instructed to extend to a specified length thereby enabling the bed frame controller 112 to control a slant angle of a corresponding portion of the bed frame 108. In one example embodiment, the bed frame adjuster 116 is instructed by the bed frame controller 112 to implement a specified configuration of the bed, such as raising the head of the bed frame 108 to a specified number of degrees, and the bed frame adjuster 116 issues control signals to one or more of the pistons to implement the specified configuration.

Figure 2:
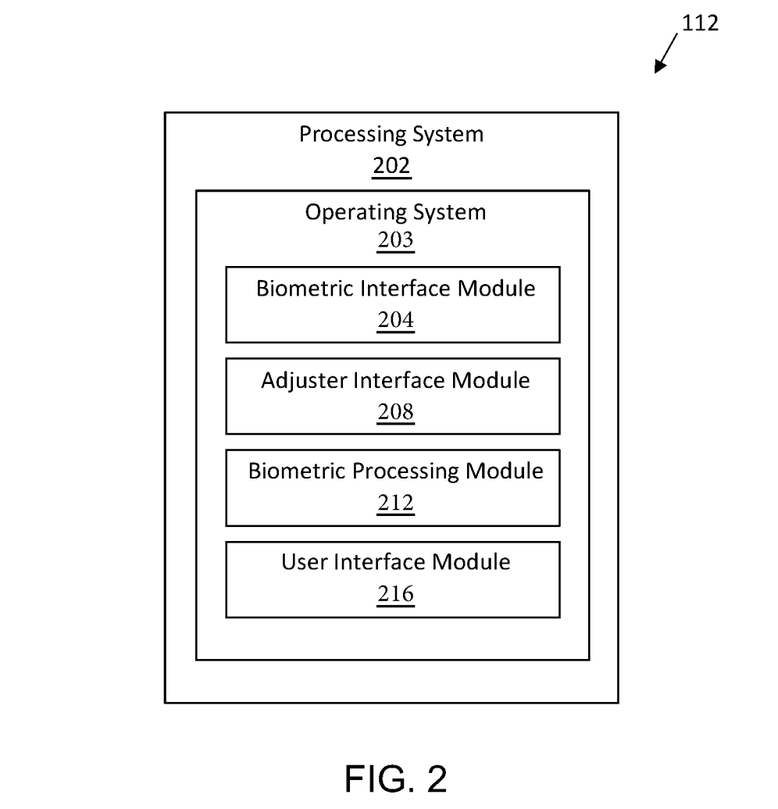
FIG. 2 is a block diagram of an example bed frame controller for adjusting a bed frame, in accordance with an example embodiment.

FIG. 2 is a block diagram of an example bed frame controller 112 for adjusting a bed frame 108, in accordance with an example embodiment. The bed frame controller 112 is shown to include a processing system 202 that may be implemented on a client or other processing device that includes an operating system 203 for executing software instructions. In accordance with an example embodiment, the bed frame controller 112 includes a biometric interface module 203, an adjuster interface module 208, a biometric processing module 212, and a user interface module 216.

The biometric interface module 204 obtains biometric information regarding a user. For example, the biometric interface module 204 may interface to a heart rate monitor to monitor a user's pulse rate. The biometric interface module 204 may interface to a microphone to detect sounds made by a user. For example, the biometric interface module 204 may detect sounds indicative of snoring. The biometric interface module 204 may interface to an oxygen monitor to determine a user's oxygen level. In one example embodiment, the biometric interface module 204 provides raw (unprocessed) or processed biometric information to the biometric processing module 212. For example, the biometric interface module 204 may provide the raw audio information from the microphone to the biometric processing module 212 or may process the raw audio information and may provide an indication to the biometric processing module 212 that snoring sounds were detected. The biometric interface module 204 is also contemplated to obtain other biometric information, including other biometric measurements. Non-limiting examples include user body temperature, user weight, user height, and the like.

The adjuster interface module 208 issues commands to the bed frame adjuster 116 that mechanically configures and/or reconfigures the bed frame 108. In one example embodiment, the adjuster interface module 208 receives status information from the bed frame adjuster 116, such as an indication of the current configuration of a pneumatic piston, an indication of the current configuration of the bed frame 108 (such as the current slant angle of a specified portion of the bed frame 108), and the like.

In one example embodiment, the adjuster interface module 208 controls a pneumatic piston of the bed frame adjuster 116 to adjust the angular slant of the head portion of the bed frame 108. In one example embodiment, the adjuster interface module 208 independently controls a plurality of pneumatic pistons, where each pneumatic piston configures a different section of the bed frame 108. In one example embodiment, the adjuster interface module 208 receives command information, such as an indication of a configuration of the bed frame 108 that is to be implemented, from the biometric processing module 212.

The biometric processing module 212 obtains biometric information and/or derivatives of the biometric information from the biometric interface module 204 and produces control information (such as commands) for the adjuster interface module 208, as described more fully below in conjunction with FIG. 3. In one example embodiment, the biometric processing module 212 also receives status information from the adjuster interface module 208, such as an indication of the current configuration of a pneumatic piston, an indication of the current configuration of the bed frame 108 (such as the current slant angle of a specified portion of the bed frame 108), and the like. For example, if the biometric information indicates that a user is suffering from an episode of sleep apnea, the head of the bed frame 108 may be incrementally raised until the biometric information indicates that the user is no longer suffering from an episode of sleep apnea. The sleep apnea may be detected, for example, by monitoring a user's oxygen levels, a user's pulse rate, sounds emitted by the user, and the like.

The biometric processing module 212 also receives configuration commands from a user via a user interface that configures the system for automatic operation, that overrides the automatic configurations and/or reconfigurations described above, and the like. For example, a user may adjust the configuration of the bed frame 108 using an up button and a down button on a user interface that raise and lower, respectively, a portion of the bed frame 108. Once adjusted, a user may select a configuration of the bed frame 108 as a neutral configuration (also referred to as a preferred configuration herein). The user may also select a predefined configuration, such as a seven degree slant, as the neutral, or preferred, configuration.

The user interface module 216 obtains configuration information for the system 100 from a user. The user interface module 216 may generate a user interface for a user to interact with, or may interface with another device, such as the user device 104, that may be used to generate a user interface for a user to interact with, as described below by way of example in conjunction with FIG. 4.

Figure 3:
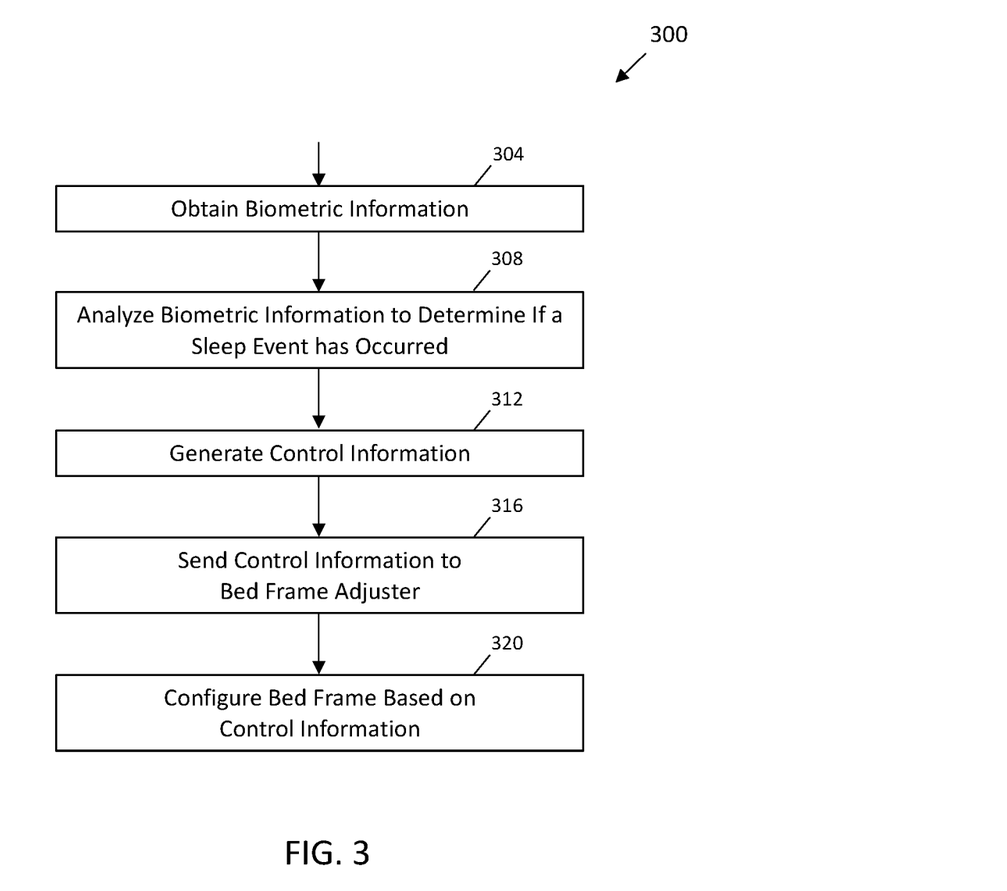
FIG. 3 is a flowchart for an example method for adjusting a bed frame, in accordance with an example embodiment.

FIG. 3 is a flowchart for an example method 300 for adjusting the bed frame 108, in accordance with an example embodiment. In one example embodiment, the bed frame adjustment method 300 may be performed by the biometric processing module 212.

In one example embodiment, biometric information is obtained (operation 304). For example, the biometric processing module 212 may obtain biometric information and/or derivatives of the biometric information from the biometric interface module 204. The biometric information may be one or more of a user's pulse rate, a user's oxygen level, a user's weight, a user's height, and the like. In one example embodiment, at least a portion of the biometric information is received from the user interface described above. For example, a user may submit their height and/or weight via the user interface.

The biometric information is analyzed to determine if a sleep event has occurred (operation 308). Non-limiting examples of a sleep event include snoring by the user, an episode of sleep apnea by the user, an occurrence of another sleep malady, and the like. For example, biometric information from the biometric interface module 204 may indicate that snoring sounds were detected by a microphone, that an absence of sound was detected, that the user's pulse rate has increased rapidly, and the like.

Control information is generated for the adjuster interface module 208 based on the results of the analysis of the biometric information (operation 312). The analysis may indicate that the bedframe 108 should be maintained in its current configuration or may specify a new configuration for the bed frame 108. The new configuration may be selected to mitigate a sleep event, such as snoring, or to reduce or cease a previously applied mitigation, such as returning the bed frame 108 to the neutral configuration after an end of a previous sleep event.

In one example embodiment, a user specifies a preferred (neutral) configuration, specifies a preferred mitigation configuration, and specifies a maximum mitigation configuration. For example, the user can position the bed frame 108 in the preferred (neutral) configuration and then notify the system 100 via a user interface to indicate that the current configuration of the bed frame 108 is the preferred (neutral) configuration. The user may select the preferred (neutral) configuration by adjusting the bed frame via up and down controls on the user interface, as described below in conjunction with FIG. 4.

The preferred mitigation configuration and the maximum mitigation configuration may be similarly selected by a user. The preferred mitigation configuration is the configuration selected by a user that is to be used to mitigate a sleep event, such as when a user is snoring, suffering from an episode of sleep apnea, exhibiting another sleep malady, and the like. The preferred mitigation configuration is the configuration that is automatically implemented, either immediately or incrementally over time, when a sleep event that is to be mitigated is detected. In one example embodiment, a plurality of mitigation configurations are selected by a user where each mitigation configuration corresponds to one or more types of sleep events and is implemented, either immediately or incrementally over time, when the corresponding sleep event is detected.

The maximum mitigation configuration indicates the most extreme positions (in comparison to the neutral configuration) that are permitted by the user, such as a maximum slant of 25 degrees. In one example embodiment, a plurality of maximum mitigation configurations are selected by the user where each maximum mitigation configuration corresponds to one or more types of sleep events and establishes a limit(s) on the amount of mitigation that may be applied. For example, maximum slants (in degrees, for example) for different sections of the bed frame 108 may be defined for each of a plurality of maximum mitigation configurations.

Time limits may also be established to limit the amount of time that a mitigation configuration and/or maximum mitigation configuration may be applied. For example, the user may specify that the head of the bed may be configured in a specified maximum mitigation configuration for up to 30 minutes.

In one example embodiment, adjustments to the bed frame 108 are limited to a maximum rate of change. For example, the adjustments may be limited to adjusting the bed frame 108 at the rate of three degrees per quarter hour. The maximum rate of change may be predefined, may be defined by the user, and the like.

In one example embodiment, the analysis of the biometric information is based on one or more predefined and/or user-defined mitigation rules. For example, a rule may indicate that, if the user is snoring, suffering from an episode of sleep apnea, exhibiting another sleep malady, or any combination thereof, the bed frame 108 is adjusted to mitigate the issue. For example, the head of the bed frame 108 may be raised by 15 degrees. The head of the bed frame 108 may be raised to a predefined or user-defined location (such as the mitigation configuration defined by the user), may be incrementally raised (such as raised by three degrees every ten minutes until the specified configuration is reached or the sleep event ends), and the like. In one example embodiment, the bed frame 108 is adjusted in an absence of a sleep malady. For example, if a portion of the bed frame 108 was raised above the neutral position and no sleep malady is detected, the bed frame 108 is adjusted toward the neutral position.

In general, based on the analysis of the biometric information, the bed frame 108 is either maintained in the current configuration, is adjusted toward a mitigation configuration, or is adjusted toward the neutral configuration. The selection of the configuration may be based on the history of the biometric information, the rate of recent adjustments, the present configuration of the bed frame 108 in relation to the neutral configuration, a history of changes to the configuration of the bed frame 108, and the like.

Non-limiting examples of the rules include the following:
if the bed frame 108 is in the neutral configuration and no sleep event is detected, the bed frame 108 is maintained in the neutral configuration;
if an adjustment of the bed frame 108 would exceed the predefined maximum rate, the bed frame 108 is not adjusted;
if an adjustment of the bed frame 108 would exceed the maximum mitigation configuration, the bed frame 108 is not adjusted away from the neutral configuration;
if an adjustment of the bed frame 108 would not exceed the predefined maximum rate, would not exceed a maximum mitigation configuration, and the biometric information indicates that snoring and/or an episode of sleep apnea occurred, the bed frame 108 is adjusted toward the mitigation configuration; and
if an adjustment of the bed frame 108 would not exceed the predefined maximum rate and the biometric information indicates that snoring and/or an episode of sleep apnea has not recently occurred, the bed frame 108 is adjusted toward the neutral configuration.

The control information is sent to the bed frame adjuster 116 (operation 316). For example, the control information can be sent to the bed frame adjuster 116 via the adjuster interface module 208. The bed frame adjuster 116 then configures the bed frame 108 in accordance with the control information (operation 320).

Figure 4:
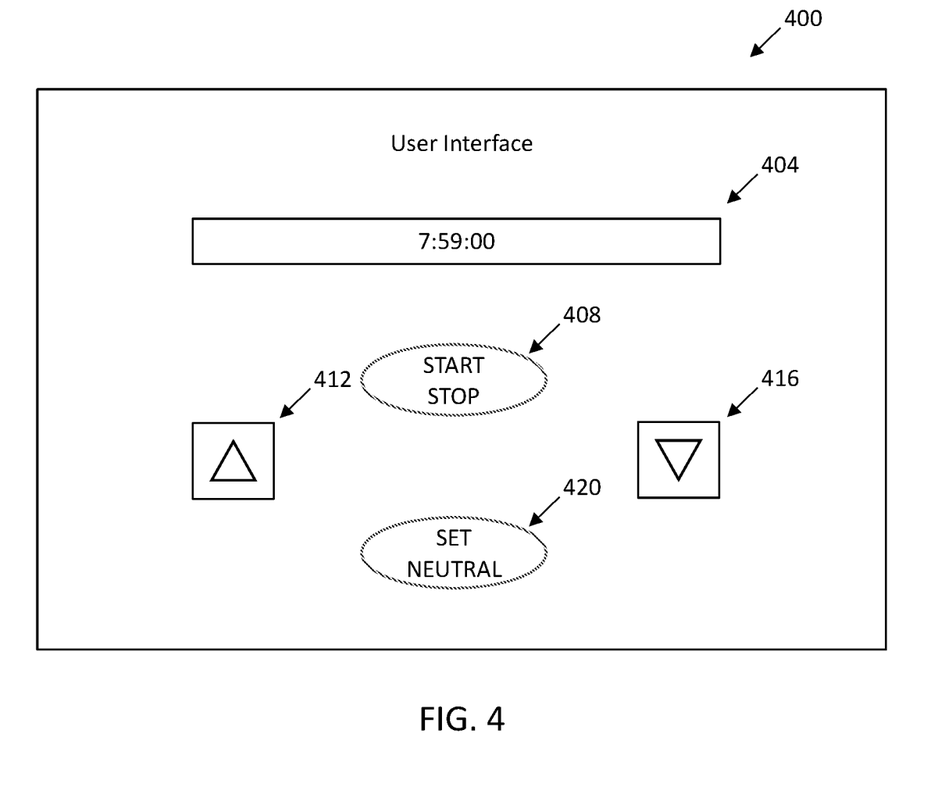
FIG. 4 is an example representation of a user interface for configuring the bed frame controller, in accordance with an example embodiment.

FIG. 4 is an example representation of a user interface 400 for configuring the bed frame controller 112, in accordance with an example embodiment. The user device 104 may generate the user interface 400, for example. A timer 408 enables a user to specify the time(s) when the bed frame controller 112 is enabled to automatically control the bed frame 108. If a user specifies a time range via the timer 408, the bed frame controller 112 will be enabled during the specified time period; otherwise, the bed frame controller 112 is enabled by selecting a start/stop button 404 and is disabled by reselecting the start/stop button 404.

A user may override the automatic adjustment of the bed frame 108 by selecting the up button 412 or down button 416 to raise or lower, respectively, a corresponding portion of the bed frame 108. Once adjusted, the user may select the set neutral button 420 to select the current configuration of the bed frame 108 to be used as the neutral (or preferred) configuration. In one example embodiment, the section of the bed frame 108 to be adjusted with the up button 412 and the down button 416 may be selected via a drop-down menu (not shown). In one example embodiment, the current configuration of the bed frame 108 may be selected to be used as the mitigation configuration. In one example embodiment, the current configuration of the bed frame 108 may be selected to be used as the maximum mitigation configuration.

Although certain examples are shown and described here, other variations exist and are within the scope of the invention. It will be appreciated by those of ordinary skill in the art that any arrangement, which is designed or arranged to achieve the same purpose, may be substituted for the specific embodiments shown. This application is intended to cover any adaptations or variations of the example embodiments of the invention described herein. It is intended that this invention be limited only by the claims, and the full scope of equivalents thereof.

Modules, Components and Logic

Certain embodiments are described herein as including logic or a number of components, modules, or mechanisms. Modules may constitute either software modules (e.g., code embodied (1) on a non-transitory machine-readable medium or (2) in a transmission signal) or hardware-implemented modules. A hardware-implemented module is a tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" should be understood to encompass a tangible entity, be that an entity that is physically constructed, permanently configured (e.g., hardwired) or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiples of such hardware-implemented modules exist contemporaneously, communications may be achieved through signal transmission (e.g., over appropriate circuits and buses that connect the hardware-implemented modules). In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation and store the output of that operation in a memory device to which it is communicatively coupled. A further hardware-implemented module may then, at a later time, access the memory device to retrieve and process the stored output. Hardware-implemented modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network 120 (e.g., the Internet) and via one or more appropriate interfaces (e.g., Application Program Interfaces (APIs).)

Electronic Apparatus and System

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium

Figure 5:
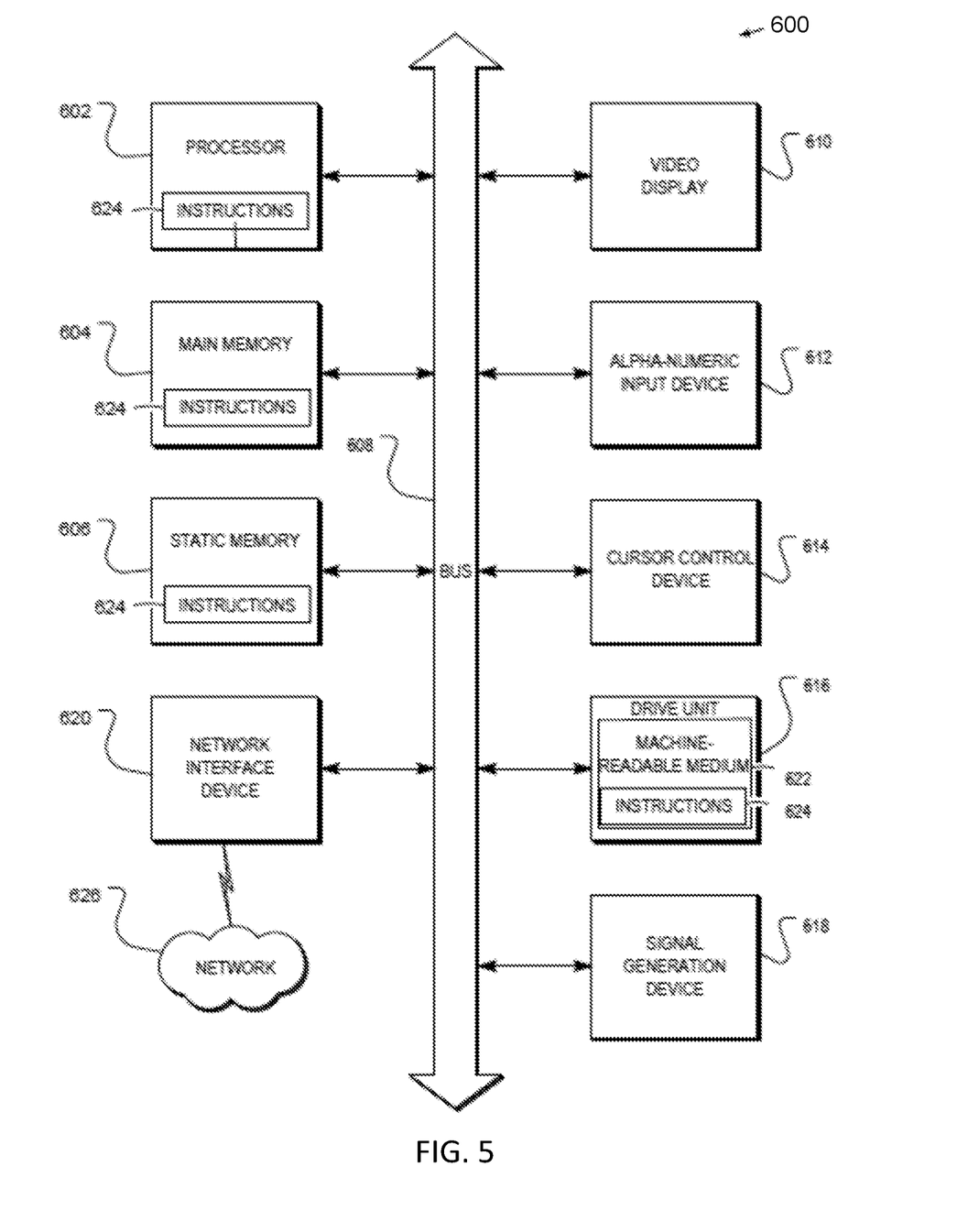
FIG. 5 is a block diagram of machine within which instructions may be executed for causing the machine to perform any one or more of the methodologies discussed herein.

FIG. 5 is a block diagram of a machine within which instructions may be executed for causing the machine to perform any one or more of the methodologies discussed herein. In one example embodiment, the machine may be the user device 104. In one example embodiment, the machine may be the bed frame controller 112. In alternative embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 600 includes a processor 602 (e.g., a central processing unit (CPU), a graphics processing unit (GPU) or both), a main memory 604 and a static memory 606, which communicate with each other via a bus 608. The computer system 600 may further include a video display unit 610 (e.g., a liquid crystal display (LCD) or a cathode ray tube (CRT)). The computer system 600 also includes an alphanumeric input device 612 (e.g., a keyboard), a user interface (UI) navigation device 614 (e.g., a mouse), a disk drive unit 516, a signal generation device 618 (e.g., a speaker) and a network interface device 620.

Machine-Readable Medium

The drive unit 616 includes a machine-readable medium 622 on which is stored one or more sets of instructions 624 and data structures (e.g., software) embodying or utilized by any one or more of the methodologies or functions described herein. The instructions 624 may also reside, completely or at least partially, within the main memory 604 and/or within the processor 602 during execution thereof by the computer system 600, the main memory 604 and the processor 602 also constituting machine-readable media. Instructions 624 may also reside within the static memory 606.

While the machine-readable medium 622 is shown in an example embodiment to be a single medium, the term "machine-readable medium" may include a single medium or multiple media (e.g., a centralized or distributed database, and/or associated caches and servers) that store the one or more instructions 624 or data structures. The term "machine-readable medium" shall also be taken to include any tangible medium that is capable of storing, encoding or carrying instructions 624 for execution by the machine and that cause the machine to perform any one or more of the methodologies of the present invention, or that is capable of storing, encoding or carrying data structures utilized by or associated with such instructions 624. The term "machine-readable medium" shall accordingly be taken to include, but not be limited to, solid-state memories, and optical and magnetic media. Specific examples of machine-readable media 622 include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; and CD-ROM and DVD-ROM disks.

Transmission Medium

The instructions 624 may further be transmitted or received over a communications network 626 using a transmission medium. The instructions 624 may be transmitted using the network interface device 620 and any one of a number of well-known transfer protocols (e.g., HTTP). Examples of communication networks include a local area network ("LAN"), a wide area network ("WAN"), the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions 624 for execution by the machine, and includes digital or analog communications signals or other intangible media to facilitate communication of such software.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method for configuring a bed frame, the method comprising:
   obtaining biometric information corresponding to a user;
   determining a bed frame configuration based on the biometric information; and
   configuring the bed frame based on the determined bed frame configuration and a detection of an absence of snoring, wherein the configuring of the bed frame adjusts the configuration of the bed frame from a mitigation configuration toward a neutral configuration in response to the biometric information indicating an absence of a sleep event that benefits from mitigation.

2. The method of claim 1, wherein the configuring the bedframe is performed in accordance with a user-defined maximum mitigation configuration.

3. The method of claim 1, further comprising adjusting the bed frame from a mitigation configuration toward the neutral mitigation configuration in response to exceeding a time limit for a configuration of the bed frame.

4. The method of claim 1, wherein the configuring the bed frame based on the determined bed frame configuration is performed by incrementally adjusting the bed frame.

5. The method of claim 1, wherein adjustments to the bed frame are limited to a user-specified maximum rate of change.

6. The method of claim 1, wherein the determining the bed frame configuration is performed by analyzing the biometric information based on one or more mitigation rules.

7. The method of claim 6, wherein the one or more mitigation rules are based on a history of the biometric information.

8. The method of claim 6, wherein the one or more mitigation rules are based on a present configuration of the bed frame in relation to the neutral configuration.

9. The method of claim 6, wherein the one or more mitigation rules are based on a history of adjustments to the configuration of the bed frame.

10. The method of claim 1, wherein the configuring of the bed frame maintains a current configuration in an absence of a sleep event, in response to at least one of an adjustment of the bed frame exceeding a predefined maximum rate and in response to the adjustment of the bed frame exceeding a maximum mitigation configuration.

11. The method of claim 1, wherein the configuring of the bed frame adjusts the configuration of the bed frame toward a mitigation configuration in response to at least one of an adjustment of the bed frame being less than a predefined maximum rate, in response to an adjustment of the bed frame being between the neutral configuration and a maximum mitigation configuration, and in response to the biometric information indicating a sleep event that benefits from mitigation.

12. An adjustable bed frame system comprising:
    a bed frame;
    a bed frame adjuster configured to mechanically configure the bed frame; and
    a bed frame controller configured to control, by sending control signals to the bedframe adjuster, a configuration of the bed frame based on an oxygen level of a user the bed frame configuration and a detection of an absence of snoring, wherein the configuring of the bed frame adjusts the configuration of the bed frame from a mitigation configuration toward a neutral configuration in response to the biometric information indicating an absence of a sleep event that benefits from mitigation.

13. The adjustable bed frame system of claim 12, wherein the bed frame controller is configured to change the configuration of the bed frame by incrementally adjusting the bed frame.

14. The adjustable bed frame system of claim 12, wherein the bed frame controller is further configured to analyze biometric information based on one or more mitigation rules.

15. The adjustable bed frame system of claim 12, wherein the bed frame adjuster comprises one or more pneumatic pistons, each pneumatic piston coupled to a different portion of the bed frame and configured to independently configure the corresponding portion of the bed frame.

16. The method of claim 1, wherein the biometric information comprises a blood pressure level of the user.

17. The method of claim 1, further comprising adjusting the bed frame from a mitigation configuration toward the neutral mitigation configuration in response to exceeding a time limit for a maximum mitigation configuration of the bed frame.

18. The method of claim 2, wherein the maximum mitigation configuration indicates a most extreme position that is specified by the user.

19. The method of claim 2, wherein the maximum mitigation configuration is one of a plurality of maximum mitigation configurations, wherein each maximum mitigation configuration corresponds to one or more types of sleep events and establishes a limit on an amount of mitigation that is permitted to be applied.

20. A method for configuring a bed frame, the method comprising:
   obtaining biometric information corresponding to a user;
   determining a bed frame configuration based on the biometric information; and
   configuring the bed frame based on the determined bed frame configuration and a detection of silence, wherein the configuring of the bed frame adjusts the configuration of the bed frame from a mitigation configuration toward a neutral configuration in response to the biometric information indicating an absence of a sleep event that benefits from mitigation.

* * * * *